United States Patent [19]

Williamson

[11] Patent Number: 4,580,561
[45] Date of Patent: Apr. 8, 1986

[54] INTERSTITIAL IMPLANT SYSTEM

[76] Inventor: Theodore J. Williamson, 2545 Mountain Laurel Way, Salem, Oreg. 97302

[21] Appl. No.: 607,174

[22] Filed: May 4, 1984

[51] Int. Cl.⁴ .............................................. A61B 17/00
[52] U.S. Cl. .................. 128/303 B; 128/1.2; 128/340; 604/116
[58] Field of Search ................ 128/303 B, 303 R, 1.2, 128/1 R, 339, 340, 346; 604/116; 33/174 D

[56] References Cited

U.S. PATENT DOCUMENTS

| | | | |
|---|---|---|---|
| 1,417,236 | 5/1922 | Evans | 33/174 D |
| 2,451,183 | 10/1948 | Tantimonaco | 604/116 |
| 2,587,966 | 3/1952 | Cleary | 128/346 |
| 2,700,385 | 1/1955 | Ortiz | 604/116 |
| 2,808,055 | 10/1957 | Thayer | 128/340 |
| 3,061,936 | 11/1962 | Dobbeleer | 33/174 D |
| 3,135,263 | 6/1964 | Connelley | 33/174 D |
| 3,508,552 | 4/1970 | Hainault | 128/303 B |
| 3,913,584 | 10/1975 | Walchle et al. | 128/305 |
| 4,086,914 | 5/1978 | Moore | 128/1.2 |
| 4,341,220 | 7/1982 | Perry | 128/303 B |
| 4,350,159 | 9/1982 | Gouda | 128/303 B |
| 4,427,005 | 1/1984 | Tener | 128/303 R |

OTHER PUBLICATIONS

"The Neurosurgical Alleviation of Parkensonism" by I. Cooper, 1956, p. 72, Lib. of Cong. #56-9108.

Primary Examiner—John J. Wilson
Attorney, Agent, or Firm—Chernoff, Vilhauer, McClung, Birdwell & Stenzel

[57] ABSTRACT

An interstitial implant system for implanting surgical instruments in body tissue comprises a planning bridge and an implant needle applicator. The planning bridge includes a pair of parallel plates positioned one on each side of the body tissue having corresponding matrices of apertures engageable by marking instruments for marking entry and exit points in the tissue thereby determining a series of linear paths. A thumb-slide actuated needle applicator has a tubular needle injector and semicircular arm providing an entry point and a target point which rest, respectively, upon the previously marked body tissue. By holding the applicator at both points, a needle inserted therein will follow the path previously determined by the entry and exit points.

7 Claims, 9 Drawing Figures

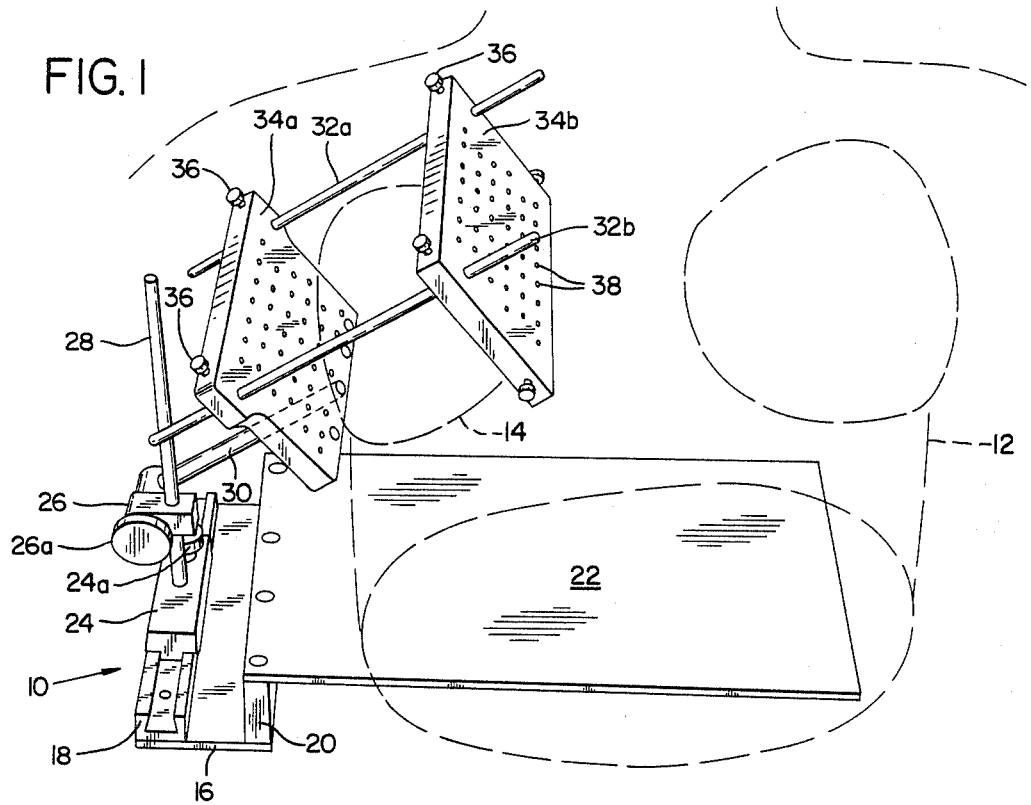
FIG. 1
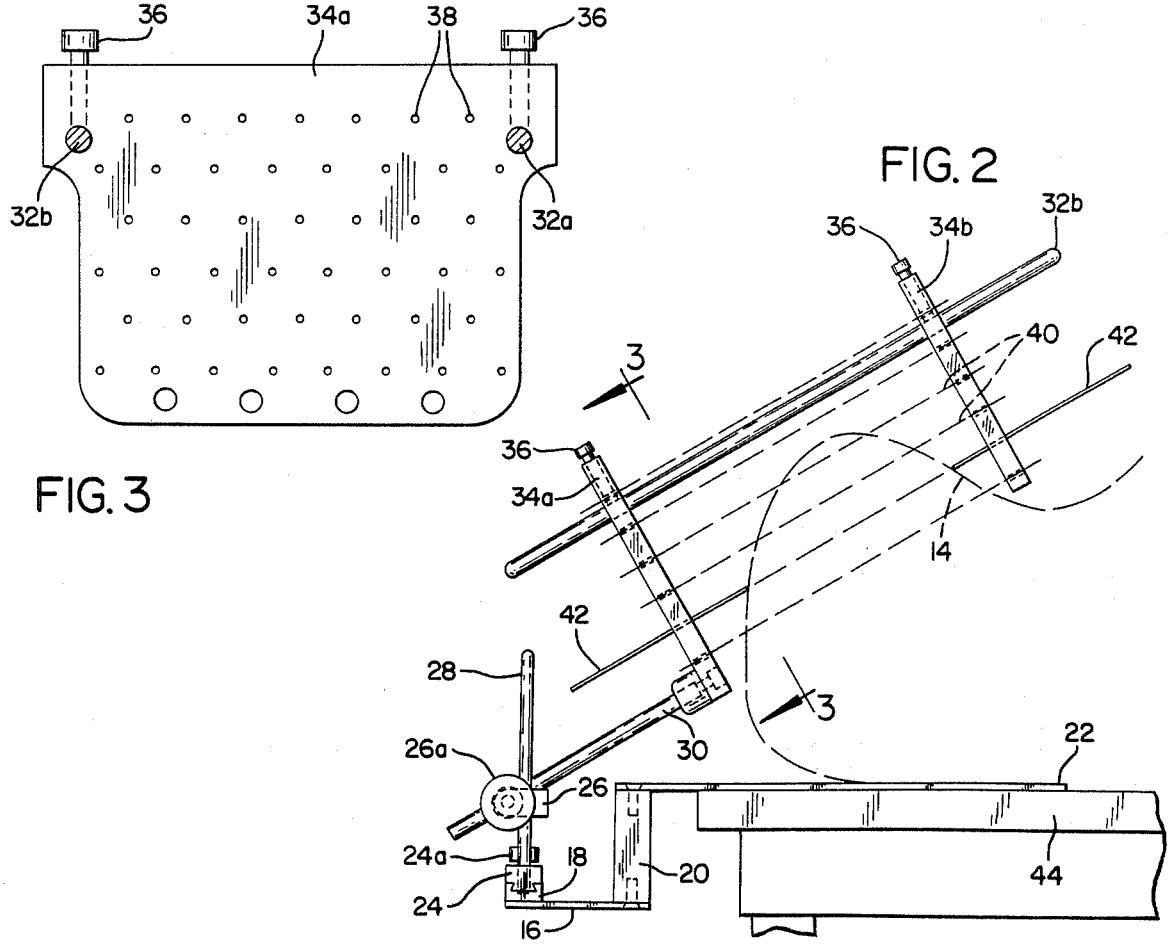
FIG. 2
FIG. 3

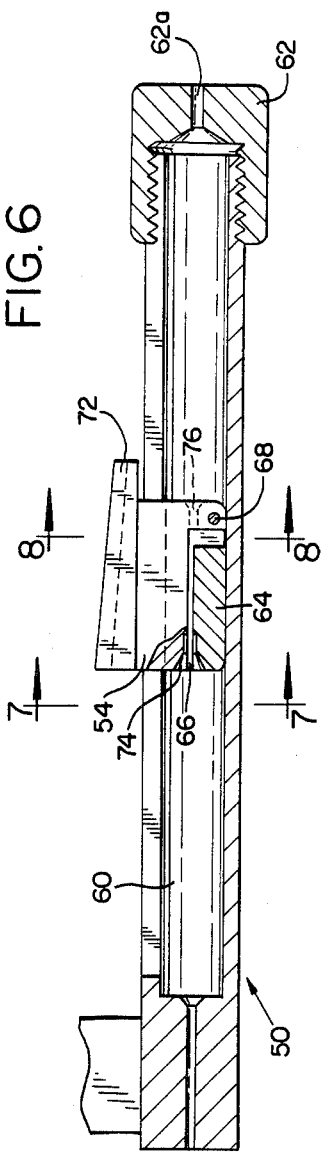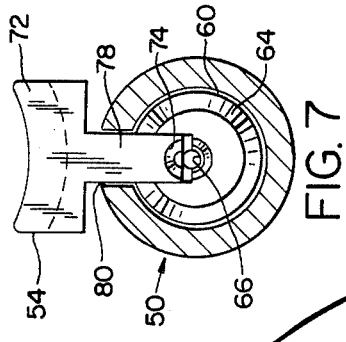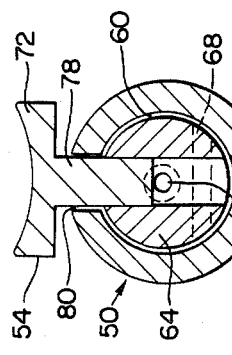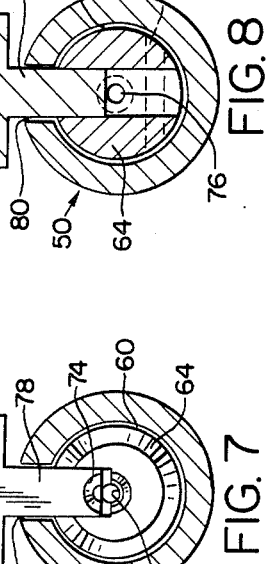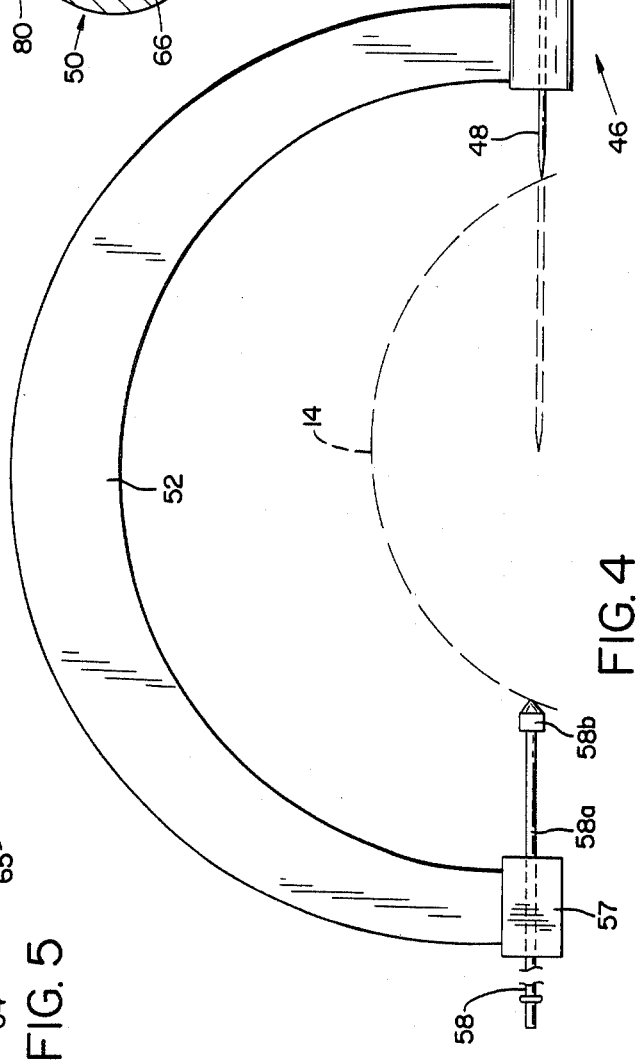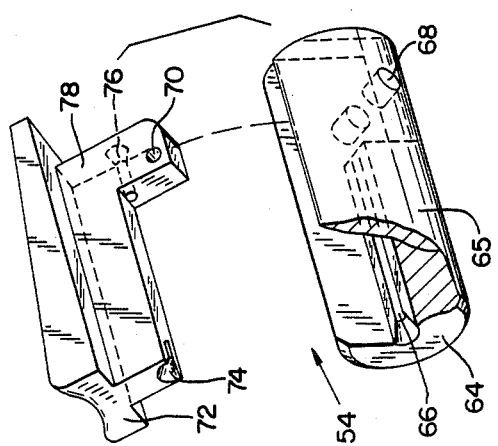

INTERSTITIAL IMPLANT SYSTEM

BACKGROUND OF THE INVENTION

The following invention relates to a method and apparatus for the precise implantation of surgical instruments, such as needles, in body tissue along a predetermined linear path.

Certain types of surgery or treatment of disease in the human body require the implantation of surgical instruments, such as needles or tubes, in body tissue along a predetermined path. For example, one method used in the treatment of breast cancer involves the irradiation of a tumor within the breast by the implantation of radioactive iridium seeds. These seeds are implanted within and around the tumor location by forcing needles through the breast tissue and using these needles to pull thin nylon tubes along the needle track into the breast. These tubes provide a pathway for inserting strings of iridium seeds. In order to effect this treatment, however, it is necessary to implant the iridium bearing tubes at precise locations within the body tissue. Moreover, in order to avoid injury to muscle tissue the needles used to implant the surgical tubes should follow a predetermined path which does not pass through such tissue.

Body tissue, however, especially in the region of the breast, is difficult to implant in this manner because of its irregular contour and the tendency of the tissue to change contour when pressure is applied. These problems are aggravated further by the fact that for this type of treatment, a plurality of needles must be implanted at predetermined locations with respect to the tumor.

These locations may be determined by viewing Computerized Axial Tomography scans and X-rays taken of the tissue, and from the scans and X-rays the entry points of the needles may be determined. Once the location for the entry point of each of these needles is chosen it then becomes necessary to insure that the path followed by the needle will result in placing the iridium bearing tubes at the proper location. Thus, although the precise location of the tumor within the body tissue can be determined by standard radiological methods, the actual planning of the path through the body tissue and the physical implementation thereof remain a problem in this type of surgery.

In the past, systems have been proposed for locating a precise point wherein the body through a combination of stereotactic methods and radiology. For example, a three dimensional stereotactic device for use in neurosurgery is shown in the Hainault patent U.S. Pat. No. 3,508,552. In Hainault, multiple pairs of parallel grids each containing a plurality of apertures are loaded with solid metal rods. The function of the parallel grids and the rods inserted therein is to provide a reference for X-rays taken of the brain. By knowing the position of the grids relative to the cranium, the precise location of the tumor may be determined from the X-rays. A similar device is shown in the Perry patent, U.S. Pat. No. 4,341,220, in which a three dimensional frame is fitted over the cranium of the patient. The frame has three plates all of which have a plurality of slots of differing length to be used as a reference against which to measure an image of a slice of the brain as would be obtained from a CAT scan.

These devices, however, are for locating a point inside the body, and not for determining the linear path of a surgical instrument to be inserted through body tissue. Moreover, neither would be suitable for this purpose. Although the Perry device shows plates having apertures, one on each side of the body tissue to be examined, the apertures are elongate slots and are not adapted to correspond with one another so as to define a straight linear path through body tissue. In Hainault, the parallel plates do contain corresponding matrices of apertures, however, both are located on the same side of the body tissue. It is impossible to determine using the Hainault device, where the exit point of an implanted needle would be so as to define a linear path.

In the treatment of tumors as described above, it is necessary not only to determine a linear path through body tissue by designating entry and exit points on the surface thereof, it is also necessary to physically implant the tubes within the body that will deliver the necessary medication. Devices have been proposed for driving needles through body tissue, but all suffer from the same defect. The problem with such devices is that they are not capable of driving a needle along a predetermined path. In these devices precise placement of the needles depends upon eye-hand coordination. Two examples of such devices are shown in the U.S. patents to Moore, U.S. Pat. No. 4,086,914 and Walchle U.S. Pat. No. 3,913,584. The Walchle device is a trigger actuated implantation device and the Moore device is actuated by twisting a handle in stepwise fashion. Neither device provides any means for determining the path through the body tissue that the needle will take.

What is needed, therefore, is a device capable of planning a path or a plurality of paths through body tissue for implantation needles or surgical instruments, and also a device capable of implanting a needle through the body tissue capable of following this predetermined path. The device must be capable of working with any body tissue regardless of its contour and deformability.

SUMMARY OF THE INVENTION

The present invention achieves these objectives and provides a means for planning and implanting surgical instruments such as needles within body tissue along a known linear path, regardless of contour and deformability, without the need for precise eye-hand coordination.

The invention comprises two parts. First an implant planning bridge is used to designate, on the body tissue to be treated, entry and exit locations for needles or other surgical devices. A linear path between each entry location and its corresponding exit location defines the line of travel through the body tissue which the surgical instrument will take. The implant planning bridge comprises a pair of parallel plates spaced apart with the body tissue to be treated interposed therebetween. The plates are connected to each other by a pair of rods which hold them in parallel relation. The plates are slidably mounted on the rods and may be adjusted for various lateral spacings therebetween. The plates each have a plurality of apertures arranged in matrices which correspond to each other so that any linear path between one aperture in a matrix and its corresponding aperture in the other matrix is perpendicular to the surfaces of both plates.

In order to position the planning bridge over selected body tissue, the plates are moveable as a unit along a track mounted to a base plate upon which the patient reclines. The plates are mounted on a post connected to the track so that they may be moved either up and down or rotationally about the axis of the post. Further degrees of freedom are provided by a mounting rod fixedly connected to one of the plates and mounted for both lateral and rotational movement with respect to the longitudinal axis of the post. The rod may also rotate about a line parallel to the axis of the track.

When the plates are positioned, one on each side of the tissue to be treated, the matrices are used for determining the entry and exit locations of the surgical instruments to be used. This is done by inserting a marking instrument through an aperture in one plate and its corresponding aperture in the opposite plate, and making a small mark on the tissue to be treated. Each aperture pair therefore defines a linear path between each such exit and entry point.

The tumor may be located within the tissue with reference to the planning bridge by inserting metal rods through selected apertures and obtaining an X-ray film of the tissue. The X-ray will usually be taken normal to the outermost plate substantially along a line parallel to the axes of the rods. The rods will be superimposed on the film appearing in projection as a series of round or elongate shadows of low X-ray density (clear or bright areas on the film) which then serve as reference points for locating the tumor with respect to the planning bridge. These images can be correlated with X-rays and computed tomography scans of the breast tissue to define tumor location. In this way aperture pairs in the bridge can be chosen for defining implantation paths which will result in the most effective treatment of the tumor.

In order to effect treatment of the tumor and implant the proper surgical instrument near its location, an implant needle applicator is used. The applicator consists of a tubular needle injector which uses a thumb-slide and brake arrangement to push a needle forward, and a substantially semicircular C-shaped arm which connects the forward end of the injector to a target end. The purpose of the C-shaped arm is to circumvent the body tissue and provide a target point which can be placed at the exit point determined by the planning bridge so that the needle is always driven from entry point to exit point along a predetermined linear path. To that end a back pointer is included in the target end of the C-shaped arm. The back pointer is an elongate cylinder having a pointed tip which may be adjusted along the same longitudinal axis as the needle to take into account the differing widths of body tissue to be treated. The thumb-slide and brake assembly grips the needle when depressed so that it cannot move in a rearward direction. Once the thumb-slide is released the thumb-slide may be moved rearwardly with respect to the needle to grip the needle at a different point where it may be depressed again to move it further into the body tissue.

It is a primary object of this invention to provide an apparatus for precisely defining a linear path through body tissue and to provide a means for physically implanting surgical instruments along that path.

It is a further object of this invention to provide an apparatus for planning the implantation of surgical instruments in body tissue by which the tissue may be marked with entry and exit points which define a plurality of linear paths through the tissue.

Yet a further object of this invention is to provide an adjustable bridge for planning the implantation of surgical instruments which may be rigidly held about the tissue to be implanted and is capable of a six-degree-of-freedom adjustment.

Yet a further object of this invention is to provide a surgical instrument applicator capable of inserting an instrument along a predetermined linear path without the need for precise eye-hand coordination.

A further object of this invention is to provide a thumb-slide actuated applicator for pushing a surgical instrument into an entry point and having a back pointer positioned at a predetermined exit point for precisely determining the correct linear path for the surgical instrument to follow.

The foregoing and other objectives, features, and advantages of the present invention will be more readily understood upon consideration of the following detailed description of the invention taken in conjunction with the accompanying drawings.

BRIEF DESCRIPTION OF THE DRAWINGS

FIG. 1 is perspective view of an implant planning bridge with the body tissue of a patient to be treated shown in phantom line.

FIG. 2 is a side elevation view of the implant planning bridge shown in FIG. 1.

FIG. 3 is a side elevation view taken along line 3—3 of FIG. 2.

FIG. 4 is a side elevation view of an implant needle applicator for use with the implant planning bridge of FIG. 1 with interior portions of the device shown in phantom line.

FIG. 5 is an exploded perspective view having a partial cutaway view of a thumb-slide and brake assembly which is a part of the implant needle applicator of FIG. 4.

FIG. 6 is a cutaway side view of the handle portion of the implant needle applicator of FIG. 4.

FIG. 7 is a sectional view taken along line 7—7 of FIG. 6.

FIG. 8 is a sectional view taken along line 8—8 of FIG. 6.

DETAILED DESCRIPTION OF THE INVENTION

Figure 2A:
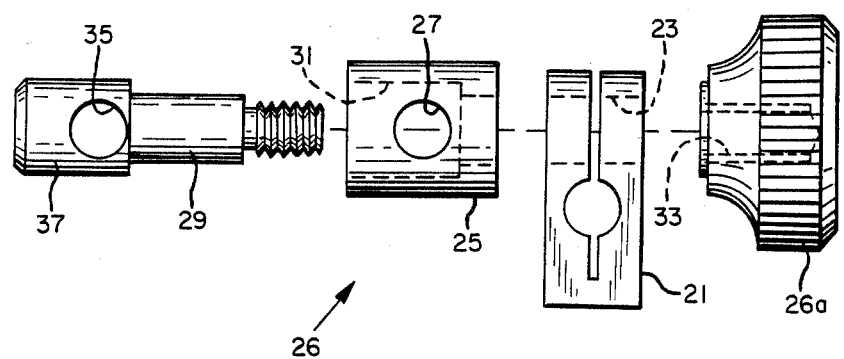
FIG. 2a is an exploded plan view of a universal joint assembly, part of the implant planning bridge shown in FIG. 1.

A patient 12 reclines on a base extension plate 22 of an implant planning bridge 10. The bridge 10 may be adjusted so that the bridge plates 34a and 34b may be placed one on each side of the body tissue 14 to be treated. The base extension plate 22 which rests on table 44 is connected to an elongate base extension post 20 which is in turn connected to a primary base 16. Primary base 16 supports a track 18 which is slideably engaged by a sliding support base 24. The sliding support base 24 has an adjustment knob 24a which frictionally engages the lower portion of track 18 to clamp the support base 24 at a desired location. Another set of adjustments is provided by universal joint 26. The universal joint 26 connects the bridge plates 34a and 34b to a vertical support post 28 via a bridge support rod 30. Both support post 28 and bridge support rod 30 slideably engage the universal joint which is tightened or loosened in its entirety by knob 26a. The bridge plates may thus rotate about the axis of support post 20 or may move vertically by raising and lowering the universal joint assembly along support post 28. The plates may also be rotated about the axis of bridge support rod 30 and rotated about an axis perpendicular to both the axis of support post 28 and bridge support rod 30.

The universal joint comprises a clamp 21 slideably mounted on support post 28. The clamp 21 has a bore 23 whose axis is perpendicular to post 28. A sleeve 25 has a bore 27 for the slideable mounting of support rod 30. A spindle 29 is inserted through a dual radius bore 31 in sleeve 25, through bore 23 and into a threaded bore 33 in locking knob 26a until a hole 35 in the spindle is aligned with bore 27. The dimensions of the bore 31 are such that the widest end 37 of the spindle 29 fits loosely within until knob 26a is tightened. Tightening knob 26a causes end 37 to move towards knob 26a which in turn creates a slight offset of hole 35 with respect to bore 27. With rod 30 inserted through hole 35 and bore 27, a frictional clamp of rod 30 is created. At the same time, sleeve 25 will be held against clamp 23 thus preventing any rotation around the axis of spindle 29, and clamp 21 will securely grip support post 28. Thus, the universal joint 26 simultaneously provides five degrees of freedom for the movement of bridge plates 34a and 34b. The lateral movement along track 18 which is the sixth degree of freedom is provided by support base 24 and knob 24a. Additionally, the distance between the plates 34a and 34b may be adjusted by loosening thumbscrews 36 and sliding plate 34b along adjustable support rods 32a and 32b.

Bridge plates 34a and 34b include a plurality of apertures 38 arranged in a matrix. Each of plates 34a and 34b have the same number of apertures and their respective matrices correspond to each other such that a line between any two corresponding apertures in plates 34a and 34b will be perpendicular to both plates and parallel to adjustable support rods 32a and 32b. These lines are shown schematically in FIG. 2 as a series of dashed lines 40.

In actual operation bridge plates 34a and 34b are adjusted so that they lie one on each side of the tissue 14 to be treated. Marking instruments 42 which may be steel rods dipped in an indelible ink are inserted through chosen pairs of corresponding apertures 38 in the bridge plates and small marks are made on the skin. The apertures 38 are bored normal to the surfaces of plates 34a and 34b which have sufficient thickness such that alignment of instruments 42 perpendicular to the surfaces of the bridge plates is automatic. These marks indicate the entry and exit points for the surgical instrument to be implanted and thus define a linear path through the body tissue to be treated.

The bridge may also be used to confirm the location of the tumor to be treated and pinpoint the location of muscle tissue to be avoided in the implantation procedure. In order to do this, metal rods are inserted into apertures at the level of the lowest plane expected to be used and an X-ray is taken with the X-ray beam axis passing through these rods and oriented at an angle matching that of the bridge (that is the angle between support post 28 and bridge support rod 30). The rods, such as rods 42, will appear on the X-ray photograph as a series of round or elongate shadows which will confirm the relationship between the position of the apertures into which rods 42 are inserted and the muscle tissue and tumor to be treated in body tissue 14.

Referring now to FIGS. 4-8, an implant needle applicator 46 comprises a needle guide handle 50, a C-shaped arm 52 and a target end 57 with a back pointer 58. A needle or other surgical instrument 48 may be loaded into the guide handle 50. Resting inside the needle guide handle 50 is a thumb-slide and brake assembly 54. The needle 48, which may be longer than the entire needle guide handle 50, may be breech loaded through an aperture 62a in a threaded end cap 62 which screws on to the end of the needle guide handle 50. The needle may then be inserted through a rear aperture 76 in the brake and thumb grip portion 72 of assembly 54. The needle rests in a semi-circular channel 66 which extends rearwardly along an interiorly raised portion 65 of the needle guide 64 of assembly 54. The needle or other surgical instrument 48 is held in position by the brake and thumb grip 72 which is pivotably connected to the needle guide 64 by hinge pins 68 cooperating with bore 70. The needle guide 64 slides within a hollow tubular channel 60 inside handle 50. Rotation of the needle guide 64 within the channel is prevented by guide bar 78 which slides longitudinally within slot 80.

As long as pressure is maintained on the brake and thumb grip 72 the assembly 54 may slide in a forward direction and will grip needle 48 thereby preventing any rearward motion. When pressure is released from the thumb grip 72, the assembly 54 may be moved to the rear to engage a different portion of needle 48.

C-shaped arm 52 connects handle 50 with a target end 57 which supports a back pointer 58. Back pointer 58 consists of an elongate rod 58a which has a bullet-shaped head 58b. The geometry of the applicator is such that needle 48 aims directly at the tip of head 58b and the axes of the needle and the back pointer are colinear.

As shown in FIG. 4, all that is necessary in order to use the needle applicator 46 is to position the head 58b on the exit point marked by marking instrument 42, place the forward end of needle 48 against the entry location and push the needle into the tissue using the thumb-slide assembly 54. Holding the applicator 46 in this position ensures that the needle will travel a predetermined path from entry point to exit point. Once the needle is in place, the thumb-slide 72 is released and the entire apparatus is slid rearwardly along the needle 48 until it is clear of the device.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. An implant planning bridge for defining a plurality of linear paths through a section of body tissue comprising:
   (a) a first planar surface having a matrix of apertures;
   (b) a second planar surface having a matrix of apertures corresponding to the matrix in the first planar surface;
   (c) means for positioning said surfaces relative to one another, one on each side of the body tissue, such that a straight linear path from an aperture on one surface to its corresponding aperture in the other surface is perpendicular to both surfaces; and
   (d) means for supporting said first and second planar surfaces relative to said body tissue and independently of said body tissue.

2. The implant planning bridge of claim 1 wherein said positioning means includes a pair of parallel rods slideably engaged by both planar surfaces, said rods providing support for at least one of said surfaces.

3. The implant planning bridge of claim 2 wherein the positioning means further includes universal joint means for adjusting the position of the planar surfaces relative to the body tissue.

4. Apparatus for planning the implantation of body tissue by a surgical instrument comprising:
   (a) a base located beneath the body tissue;
   (b) a track extending along an edge parallel to said base;
   (c) a support post adapted to slidably engage said track and capable of movement thereon;
   (d) universal joint means adapted to slidably engage said post, said means including means for simultaneously providing five degrees of freedom of movement for a bridge means; and
   (e) wherein said bridge means is connected by a support rod to said universal joint means for defining a plurality of linear paths through said body tissue.

5. The apparatus of claim 4 wherein said bridge means includes a pair of parallel plates having corresponding matrices of apertures.

6. A method of planning the implantation of body tissue by a surgical instrument comprising the steps of:
   (a) positioning one each of a pair of parallel planar surfaces having corresponding matrices of apertures defining a series of rectilinear paths between said surfaces on each side of the body tissue to be implanted;
   (b) marking an entry point for the surgical instrument on one side of the body tissue by inserting a marking instrument through an aperture in one of said planar surfaces; and
   (c) marking an exit point for the surgical instrument on the other side of the body tissue by inserting a marking instrument in the corresponding aperture on the opposite planar surface.

7. The method of claim 6 further including inserting a plurality of rods substantially opaque to X-radiation in apertures selected to define points indicative of a location within the body tissue and taking an X-ray photograph of the body tissue substantially along the axes of the rods.

* * * * *